United States Patent
Busa et al.

(10) Patent No.: US 11,604,191 B2
(45) Date of Patent: Mar. 14, 2023

(54) METHODS FOR ISOLATING TARGET CELLS FROM BLOOD

(71) Applicants: William Busa, Rancho Cordova, CA (US); Philip H. Coelho, Rancho Cordova, CA (US); Jonathan Ellis, Rancho Cordova, CA (US); Dalip Sethi, Rancho Cordova, CA (US)

(72) Inventors: William Busa, Rancho Cordova, CA (US); Philip H. Coelho, Rancho Cordova, CA (US); Jonathan Ellis, Rancho Cordova, CA (US); Dalip Sethi, Rancho Cordova, CA (US)

(73) Assignee: THERMOGENESIS CORPORATION, Rancho Cordova, CA (US)

( * ) Notice: Subject to any disclaimer, the term of this patent is extended or adjusted under 35 U.S.C. 154(b) by 0 days.

(21) Appl. No.: 16/556,632

(22) Filed: Aug. 30, 2019

(65) Prior Publication Data
US 2020/0072834 A1 Mar. 5, 2020

Related U.S. Application Data

(60) Provisional application No. 62/725,750, filed on Aug. 31, 2018.

(51) Int. Cl.
*G01N 33/569* (2006.01)
*B01D 21/26* (2006.01)
*G01N 33/543* (2006.01)

(52) U.S. Cl.
CPC ..... *G01N 33/56972* (2013.01); *B01D 21/262* (2013.01); *G01N 33/5432* (2013.01); *G01N 33/54333* (2013.01); *G01N 33/56966* (2013.01); *G01N 2333/7051* (2013.01)

(58) Field of Classification Search
CPC ......... G01N 33/56966; G01N 33/5432; G01N 33/54333; G01N 33/56972; G01N 2333/7051
See application file for complete search history.

(56) References Cited

U.S. PATENT DOCUMENTS

2015/0219636 A1* 8/2015 Rychak ............. G01N 33/5432
435/5

FOREIGN PATENT DOCUMENTS

WO WO 2017/117349 * 7/2017 ............. G01N 33/53

OTHER PUBLICATIONS

Liou et al. Buoyancy-Activated Cell Sorting Using Targeted Biotinylated Albumin Microbubbles PLoS ONE 10(5): e0125036. pp. 1-15 (May 20, 2015).*
Xiaoyu Shi. Buoyancy-based separation of antigen-specific T cells. University of California San Diego Electronic Theses and Dissertations. Retrieved from https://escholarship.org/uc/item/9g97509x. Abstract Only (2016).*
Hsu et al. Isolating Cells from Blood Using Buoyancy Activated Cell Sorting (BAGS) with Glass Microbubbles. 14th International Conference on Miniaturized Systems for Chemistry and Life Sciences. Groningen, The Netherlands (Oct. 3-7, 2010).*
Mix-All Laboratory Tube Mixer, RPI, from http://web.archive.org/web/20061231202937/http://www.rpicorp.cp:80/products/ ... printed on Oct. 11, 2021.

* cited by examiner

*Primary Examiner* — Gailene Gabel
(74) *Attorney, Agent, or Firm* — McDonnell Boehnen Hulbert & Berghoff

(57) ABSTRACT

Disclosed herein are methods for isolating target cells from blood, involving mixing in an open container an undiluted blood sample having a volume of 10 ml or less, and binding agents, wherein each binding agent comprises (A) a primary binding agent comprising an agent capable of binding to at least one cellular epitope on target cells in the undiluted blood sample, (B) a first linker bound to the primary binding agent, to generate binding agent-attached target cells in the undiluted blood sample; contacting the binding agent-attached target cells in the undiluted blood sample with a plurality of buoyant reagents that include a second linker capable of binding to the first linker to generate an undiluted buoyant reagent-attached target cell mixture; diluting the undiluted buoyant reagent-attached target cell mixture by at least 20% to produce a diluted buoyant reagent-attached target cell mixture; applying a vectorial force, such as centrifugal force, to the diluted buoyant reagent-attached target cell mixture to generate a stratified diluted buoyant reagent-attached target cell mixture; removing the buoyant reagent-attached target cells from the stratified diluted buoyant reagent-attached target cell mixture; and isolating the target cells from the buoyant reagent-attached target cells.

22 Claims, 2 Drawing Sheets

METHODS FOR ISOLATING TARGET CELLS FROM BLOOD

CROSS REFERENCE

This application claims priority to U.S. Provisional Patent Application Ser. No. 62/725,750 filed Aug. 31, 2018, incorporated by reference herein in its entirety

BACKGROUND

Basic research in fields as diverse as immunology, stem cell biology, tissue engineering, infectious disease biology, physiology, biophysics, molecular genetics, and pathology routinely involves work with freshly isolated cells from volunteer donors' blood. Frequently these are small-volume preparations (often fewer than a million cells), produced from small freshly-drawn phlebotomy specimens (on the order of 10 mL of blood or less). Increasingly, the researcher will seek to isolate a single molecularly specific cell type, usually based on the desired cell type's surface immunophenotype (as opposed to a mixed cell-type preparation such as peripheral blood mononuclear cells—so-called 'PBMC preps').

The basic researcher's need to prepare such target cell isolates from small sample volumes, quickly and at minimal cost and investment, often renders the most sophisticated cell isolation methods in use today less than ideally suited to her needs. Existing methods suffer from defects including being very expensive, very slow throughput, yielding target cell recoveries and purities that are insufficient to the researcher's needs, and/or an inability to isolate target cells from whole blood, requiring instead time-consuming initial steps of red cell depletion and PBMC preparation prior to target cell isolation. Thus there exists an unmet need for a research-scale blood cell isolation method featuring low cost and capital intensity, rapid throughput, high target cell recovery and purity, suitable for use on whole blood samples of less than milliliters without preliminary PBMC preparation and/or red cell depletion.

SUMMARY

In one aspect are disclosed methods for isolating target cells from blood, comprising:
  (a) mixing in an open container
    (i) an undiluted blood sample having a volume of 10 ml or less, and
    (ii) binding agents, wherein each binding agent comprises
      (A) a primary binding agent comprising an agent capable of binding to at least one cellular epitope on target cells in the undiluted blood sample, (B) a first linker bound to the primary binding agent,
    wherein the mixing occurs for a time and under conditions suitable to promote binding of the primary binding agents to the target cells to generate binding agent-attached target cells in the undiluted blood sample;
  (b) contacting the binding agent-attached target cells in the undiluted blood sample with a plurality of buoyant reagents, wherein each buoyant reagent comprises a second linker bound to the buoyant reagent, wherein the second linker is capable of binding to the first linker, wherein the contacting occurs for a time and under conditions suitable to promote binding of the second linker to the first linker to generate an undiluted buoyant reagent-attached target cell mixture;
  (c) diluting the undiluted buoyant reagent-attached target cell mixture by at least 20% to produce a diluted buoyant reagent-attached target cell mixture;
  (d) applying a vectorial force, such as centrifugal force, to the diluted buoyant reagent-attached target cell mixture to generate a stratified diluted buoyant reagent-attached target cell mixture;
  (e) removing the buoyant reagent-attached target cells from the stratified diluted buoyant reagent-attached target cell mixture; and
  (f) isolating the target cells from the buoyant reagent-attached target cells.

In one embodiment, the buoyant reagents comprise gas-filled bubbles. In another embodiment, the gas-filled bubbles comprise perfluorocarbon gas cores encompassed by lipid or phospholipid shells. In a further embodiment, the gas-filled bubbles have a mean size volume of greater than 6 $\mu m^3$ and less than 10 $\mu m^3$. In one embodiment, the gas-filled bubbles have a mean size diameter of between 1.5 $\mu m$ and about 3 $\mu m$. In another embodiment, the gas-filled bubbles are present in the contacting step at a concentration of at least $4\times10^8$ per ml. In one embodiment, the second linker comprises streptavidin (SA), and the first linker comprises biotin. In various further embodiments, the streptavidin is present on the buoyant reagent at a density of greater than 20,000, 25,000, or 26,000 molecules per $um^2$. In one embodiment, the binding agents comprise antibodies attached to the first linker. In various embodiments, the undiluted blood sample has a volume of 5 ml or less, 3 ml or less, or 1 ml to 3 ml.

In one embodiment, the diluting comprises diluting the undiluted buoyant reagent-attached target cell mixture by between 20% and 500% to produce the diluted buoyant reagent-attached target cell mixture. In another embodiment, the removing step comprises removing the buoyant reagent-attached target cells from the stratified diluted buoyant reagent-attached target cell mixture using a pipette or syringe. In a further embodiment, the isolating step comprises isolating the target cells from the buoyant reagent-attached target cells by sonicating or applying positive pressure to degas the microbubbles.

In one embodiment, the target cells comprise cells of surface phenotypes including one or more of CD45+, CD3+, CD4+, CD8+, CD25+, CD14+, CD16+, CD19+, CD56+, CD34+, CD117+, CD235a, CD349⁻, T cell receptor (TCR) alpha, gamma, beta & delta cells. In another embodiment, the target cells comprise $CD3^+$. In other embodiments, the target cells are isolated with a purity of at least 85% or at least 90%. In further embodiments, the target cells are isolated with a viability of at least 80% or at least 90%. In still further embodiments, at least 50% or at least 70% of the target cells in the blood sample are isolated. In another embodiment, the target cells are not platelets or red blood cells.

DETAILED DESCRIPTION

Figure 1:
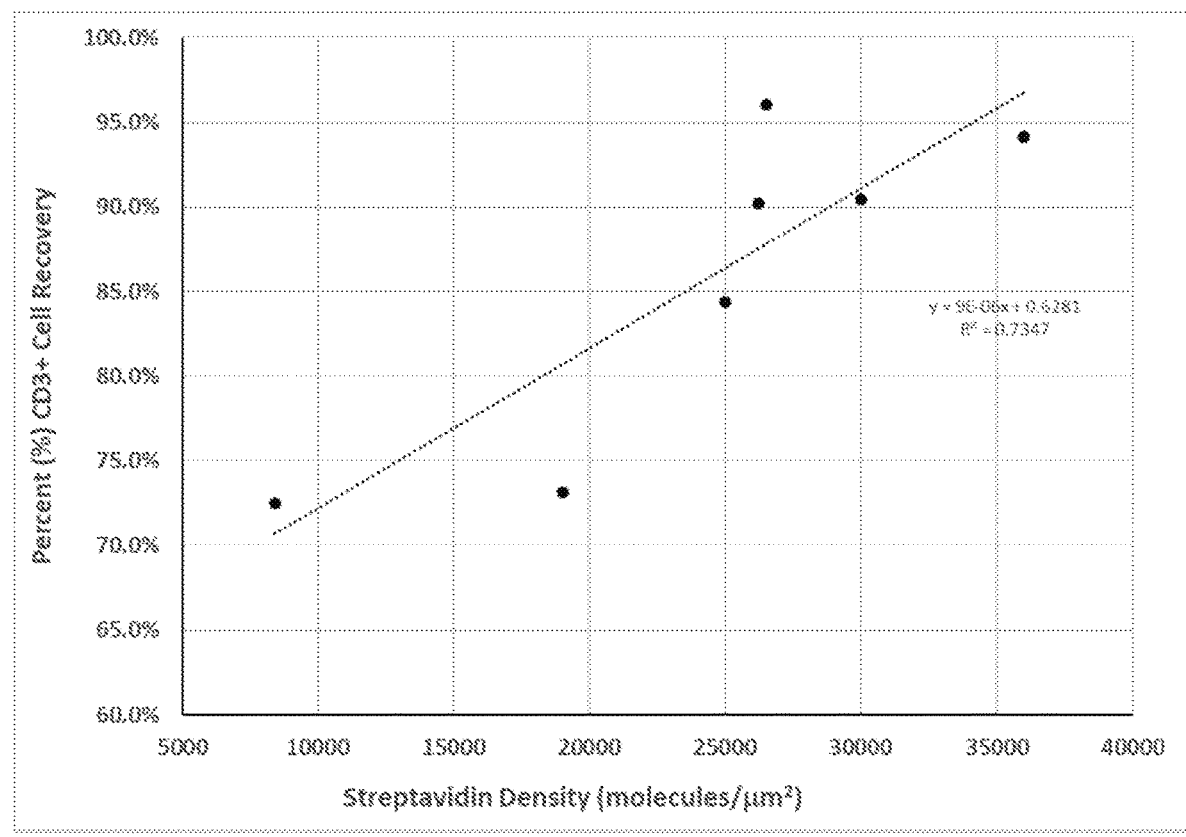
FIG. 1 is a graph showing an exemplary correlation of streptavidin density (molecules/$\mu m^2$) of microbubbles (buoyant) reagent to percent (%) recovery of target CD3+ cells.

As used herein, the singular forms "a", "an" and "the" include plural referents unless the context clearly dictates otherwise. "And" as used herein is interchangeably used with "or" unless expressly stated otherwise.

As used herein, the term "about" means +/−5% of the recited parameter.

All embodiments of any aspect of the disclosure can be used in combination, unless the context clearly dictates otherwise.

Unless the context clearly requires otherwise, throughout the description and the claims, the words 'comprise', 'comprising', and the like are to be construed in an inclusive sense as opposed to an exclusive or exhaustive sense; that is to say, in the sense of "including, but not limited to". Words using the singular or plural number also include the plural and singular number, respectively. Additionally, the words "herein," "above," and "below" and words of similar import, when used in this application, shall refer to this application as a whole and not to any particular portions of the application.

The description of embodiments of the disclosure is not intended to be exhaustive or to limit the disclosure to the precise form disclosed. While the specific embodiments of, and examples for, the disclosure are described herein for illustrative purposes, various equivalent modifications are possible within the scope of the disclosure, as those skilled in the relevant art will recognize.

In one aspect are provided methods for isolating target cells from blood, comprising:
  (a) mixing in an open container
    (i) an undiluted blood sample having a volume of 10 ml or less, and
    (ii) binding agents, wherein each binding agent comprises (A) a primary binding agent comprising an agent capable of binding to at least one cellular epitope on target cells in the undiluted blood sample, (B) a first linker bound to the primary binding agent, wherein the mixing occurs for a time and under conditions suitable to promote binding of the primary binding agents to the target cells to generate binding agent-attached target cells in the undiluted blood sample;
  (b) contacting the binding agent-attached target cells in the undiluted blood sample with a plurality of buoyant reagents, wherein each buoyant reagent comprises a second linker bound to the buoyant reagent, wherein the second linker is capable of binding to the first linker, wherein the contacting occurs for a time and under conditions suitable to promote binding of the second linker to the first linker to generate an undiluted buoyant reagent-attached target cell mixture;
  (c) diluting the undiluted buoyant reagent-attached target cell mixture by at least 20% to produce a diluted buoyant reagent-attached target cell mixture;
  (d) applying a vectorial force, such as centrifugation, to the diluted buoyant reagent-attached target cell mixture to generate a stratified diluted buoyant reagent-attached target cell mixture;
  (e) removing the buoyant reagent-attached target cells from the stratified diluted buoyant reagent-attached target cell mixture; and
  (f) isolating the target cells from the buoyant reagent-attached target cell mixture.

The methods of the invention provide significant improvements in isolating specific subsets of blood cells of very high purity and viability using relatively simple reagents and small volumes, and thus are particularly suitable for use in small-scale laboratory and research use.

The methods are carried out in an open container, thus obviating the need for expensive and complex devices for blood cell isolation. As used herein, an "open" container is one that is not hermetically sealed and is often accessed aseptically in a laminar flow hood. The "open" containers are commonly used in handling small blood volumes such as vacutainers or 1 mL or 2 mL or 5 mL or 10 mL or 15 mL or 50 mL plastic tubes.

The blood from which target cells are to be isolated is undiluted blood sample (i.e.: whole blood or peripheral blood) having a volume of 10 ml or less. Any such target cells from the undiluted blood sample may be targeted, including but not limited to cells of surface immunophenotypes comprising one or more of CD45+, CD3+, CD4+, CD8+, CD25+, CD14+, CD16+, CD19+, CD56+, CD34+, CD117+, CD235a, CD349−, T cell receptor (TCR) alpha, gamma, beta & delta. In one specific embodiment, red blood cells and platelets are not targeted (i.e.: the target cells are not platelets or red blood cells). In a specific embodiment, the target cells comprise $CD3^+$ cells.

As described in the examples that follow, the inventors have demonstrated that the methods disclosed herein can be used to isolate target cells with purity and viability of greater than 80% (mean 94%) and in most cases of greater than 90% (mean 95%), with an average target cell recovery of at least 70%, with a mean recovery of 85%.

In various embodiments, the undiluted blood sample from which a specific subset of cells are to be isolated is between about 0.1 ml to 10 ml, between about 0.1 ml to about 7.5 ml, between about 0.1 ml to about 5 ml, between about 0.1 ml to about 3 ml, between about 0.5 ml to 10 ml, between about 0.5 ml to about 7.5 ml, between about 0.5 ml to about 5 ml, between about 0.5 ml to about 3 ml, between about 1 ml to 10 ml, between about 1 ml to about 7.5 ml, between about 1 ml to about 5 ml, between about 1 ml to about 3 ml, 0.1, 0.25 ml, 0.5 ml, 0.75 ml, 1 ml, 1.5 ml, 2 ml, 2.5 ml, 3 ml, 3.5 ml, 4 ml, 4.5 ml, 5 ml, 5.5 ml, 6 ml, 6.5 ml, 7 ml, 7.5 ml, 8 ml, 8.5 ml, 9 ml, 9.5 ml, or 10 ml. The blood may be obtained from any organism of interest, including but not limited to human, rodent (i.e., mouse, rat, hamster, etc.), rabbit, pig, goat, monkey, sheep, horse, bovine, etc. In one specific embodiment, the blood is of human origin.

As used herein, a "binding agent" is a structure, such as a molecule, that is capable of binding with sufficiently high affinity and specificity to at least one cellular epitope on target cells in blood. Suitable binding agents may include, without limitation, antibodies, oligonucleotides, aptamers, molecularly imprinted polymers, carbohydrates, proteins, peptides, enzymes, small molecules, lipids, fatty acids, metal atoms, metal ions and synthetic polymers. In one specific embodiment, the binding agent comprises one or more antibodies that selectively bind to a cellular epitope on the target cells in blood. The choice of the one or more antibodies will depend on the target cell(s) of interest in the blood sample.

As used herein, the "first linker" and "second linker" comprises a pair of chemical moieties attached covalently or non-covalently one to a binding agent (first linker) the other to a buoyant reagent (second linker), which are able to spontaneously attach (either covalently or non-covalently) to each other in a suitable medium under suitable conditions with sufficiently high affinity to achieve the indirect connection of a binding agent to a buoyant reagent, via the linkers, to form an undiluted buoyant reagent-attached target cell mixture. In one embodiment, the first linker comprises biotin; in one such embodiment, the binding molecules comprise biotin covalently bound to an antibody. In this embodiment, the second linker generally comprises streptavidin. In other specific embodiments, the first linker is a first oligonucleotide and the second linker is a second oligonucleotide complementary over at least a portion of its length (such as fully complementary) to the first oligonucleotide and capable of binding to the first oligonucleotide via base pairing.

In certain embodiments, the quantity of the binding agents added to the undiluted blood is sufficient to substantially saturate the binding agent's binding sites on the target cells while leaving only an amount of unbound binding agent remaining in the mixture that is insufficient to substantially interfere with the binding of buoyant reagent to the first linker. In further embodiments, the quantity of the binding agents to add to the undiluted blood is determined by a preceding count of the number of target cells present in the undiluted blood, employing any suitable means known to those skilled in the art, for example, without limitation a hematology analyzer, flow cytometry, microscopy, sedimentation, enzymatic assay, ELISA, or the like. In certain embodiments, the quantity of the one or more binding agents to add to the undiluted blood is determined by testing a range of two or more concentrations of binding agents against aliquots of the undiluted blood. In further embodiments, the quantity of the one or more binding agents used is up to 40 times the number of binding agent binding sites present on the target cells.

As used herein a "buoyant reagent" is a material that has a density substantially different from the density of target cells alone and/or the density of blood. Suitable buoyant reagents may include, without limitation, gas-encapsulating bubbles with protein or lipid shells, hollow polymers, glass beads (either hollow or solid), microporous beads with entrained gas, droplets of an immiscible liquid, gold nanoparticles, and silver nanoparticles. In one specific embodiment, the buoyant labels comprise gas-filled bubbles, such as those encompassed by protein, lipid, phospholipid, or carbohydrate shells. In one embodiment, the gas-filled bubbles comprise perfluorocarbon gas cores encompassed by a phospholipid or lipid shell.

The buoyant reagent may have any suitable diameter; in one non-limiting embodiment, the gas-filled bubbles have a mean size diameter of at least 1.5 μm. The inventors have demonstrated that specific embodiments of the buoyant reagents, binding agents, and linkers provide significantly improved results on parameters including but not limited to cell recovery, purity, viability, and activity.

In one specific embodiment, the gas-filled bubbles (such as perfluorocarbon gas cores encompassed by a phospholipid or lipid shell) have a mean size volume of greater than 6 $\mu m^3$ and less than 10 $\mu m^3$. In various embodiments, the gas-filled bubbles (such as perfluorocarbon gas cores encompassed by a phospholipid or lipid shell) have a mean size volume of between about 6.2 $\mu m^3$ to about 9.9 $\mu m^3$, about 6.5 $\mu m^3$ to about 9.5 $\mu m^3$, about 7 $\mu m^3$ to about 9 $\mu m^3$, or about 7 $\mu m^3$ to about 8.5 $\mu m^3$.

In another specific embodiment, the gas-filled bubbles (such as perfluorocarbon gas cores encompassed by a phospholipid or lipid shell) have a mean size diameter of greater than 1.5 μm. In various further embodiments, the gas-filled bubbles (such as perfluorocarbon gas cores encompassed by a phospholipid or lipid shell) have a mean size diameter of greater than 1.5 μm to about 3 μm. In other embodiments, the gas-filled bubbles (such as perfluorocarbon gas cores encompassed by a phospholipid or lipid shell) have a mean size diameter of between about 1.6 μm to about 2.9 μm, between about 1.7 μm to about 2.8 μm, or between about 1.8 μm to about 2.7 μm.

In one specific embodiment, the gas-filled bubbles (such as perfluorocarbon gas cores encompassed by a phospholipid or lipid shell) are present in the contacting step at a concentration of at least $4 \times 10^8$ per ml. In various embodiments, the gas-filled bubbles (such as perfluorocarbon gas cores encompassed by a phospholipid or lipid shell) are present in the contacting step at a concentration of between $4 \times 10^8$ per ml and about $12 \times 10^8$ per ml, between $4 \times 10^8$ per ml and about $11 \times 10^8$ per ml, or between $4 \times 10^8$ per ml and about $8.5 \times 10^8$ per ml.

In another specific embodiment, the second linker, such as streptavidin (SA) or the second member of an oligonucleotide pair with the first linker, is present on the buoyant reagent (such as perfluorocarbon gas cores encompassed by a phospholipid or lipid shell) at a density of at least 20,000 molecules per $um^2$. In another embodiment, the streptavidin or other second linker is present on the buoyant reagent (such as perfluorocarbon gas cores encompassed by a phospholipid or lipid shell) at a density of at least 20,000; 21,000; 22,000, 23,000, 24,000, 25,000; 26,000; 27,000; 28,000; 29,000; or 30,000 molecules per $um^2$. In various further embodiments, the streptavidin or other second linker is present on the buoyant reagent (such as perfluorocarbon gas cores encompassed by a phospholipid or lipid shell) at a density of between about 20,000; 21,000; 22,000, 23,000, 24,000, 25,000; 26,000; 27,000; 28,000; 29,000; or 30,000 molecules and about 40,000 molecules per $um^2$.

The mixing and contacting steps are carried out for a time and under conditions to promote the recited binding events. Any suitable conditions to promote such mixing and contacting may be used, and it is within the level of those of skill in the art to determine such appropriate conditions as temperature, length of incubation, application of stirring or other mixing forces, medium to be used, wash steps to incorporate, etc., based on the teachings herein. Non-limiting embodiments are described in detail herein.

The undiluted buoyant reagent-attached target cell mixture is diluted after step (b) by at least 20% to produce a diluted buoyant reagent-attached target cell mixture to facilitate separation of the attached cells from non-attached cells in the blood. In various embodiments, the dilution is between 20% and about 500%; in various other embodiments, between 20% and about 450%, 400%, 350%, 300%, 250%, 200%, 200%, 150%, or 100% to produce the diluted buoyant reagent-attached target cell mixture.

A vectorial force is then applied to the diluted buoyant reagent-attached target cell mixture to generate a stratified diluted buoyant reagent-attached target cell mixture. A "vectorial force" is a force having a direction as well as a magnitude, including but not limited to gravitational force, centripetal force, and centrifugal force. In one specific embodiment, the vectorial force comprises a centrifugal force generated via centrifugation.

The buoyant reagent-attached target cells are then removed from the stratified diluted buoyant reagent-attached target cell mixture using any suitable procedure, including but not limited to removal using a pipette or syringe.

The target cells are then isolated from the buoyant reagent-attached target cells using any suitable means to detach the buoyant reagents from the target cells. Such methods include, but are not limited to sonicating or applying positive pressure to degas or collapse the microbubbles.

EXAMPLES

Figure 2:
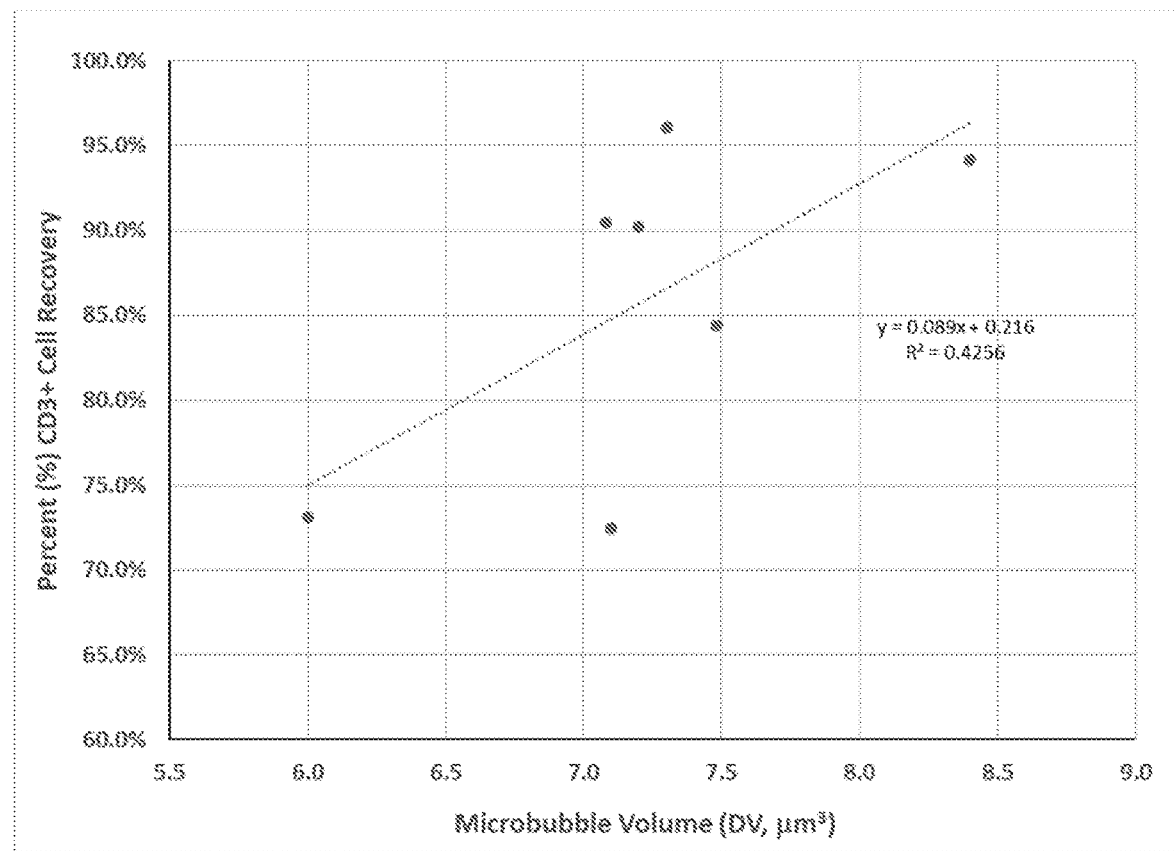
FIG. 2 is a graph showing an exemplary correlation of microbubbles (buoyant) reagent volume to percent (%) recovery of target CD3+ cells

Example 1. Identification of Physicochemical Characteristics of Microbubble Reagent that Provide Improved CD3+ Cell Recovery The physicochemical characteristics microbubble reagent was obtained and correlation with CD3+ cell recovery from a mixture of blood cell populations was studied. In brief, cell mixture of mononucleated cells with few granulocytes and red blood cells was obtained. The cell mixture was incubated with 0.875 µg of CD3-Biotin antibody (clone UCHT1; available from a number of suppliers) followed by streptavidin-coated buoyant microbubble reagent. Following incubation, the mixture was centrifuged at 400×g for 5 min. at room temperature. The buoyant reagent-attached target cells were removed from the tube using a pipette. The fraction was degassed using a 10-mL syringe to apply slight positive pressure to irreversibly collapse the buoyant reagent. Table 1 shows the physicochemical characteristics of the reagent and CD3+ cell recoveries obtained. To study correlation between the physicochemical properties of microbubble reagent and performance, percent (%) CD3+ cell recovery, regression analysis were performed. Positive correlation was observed between streptavidin density on microbubble reagent and CD3+ cell recovery (FIG. 1). Positive correlation was also observed between mean volume of microbubble reagent, an indicator of buoyancy, and CD3+ cell recovery (FIG. 2).

Example 2. Isolation of CD3+ Target Cells from Undiluted Whole Blood

Whole human peripheral blood was purchased. A small volume, 1 mL or 3 mL or 5 mL, of undiluted whole peripheral blood was incubated with CD3-Biotin antibody for 30 min. at room temperature. Following antibody incubation, streptavidin-coated microbubble reagent was added to the tube and incubated for 20 min. at room temperature. Following microbubble incubation, a buffer was added to dilute and increase the volume. The tubes were centrifuged at 400×g for 7.5 min. The buoyant reagent-attached target cells were removed from the tube using a pipette. The fraction was degassed using a 10-mL syringe to irreversibly collapse the buoyant reagent. Table 2 shows the CD3+ cell recoveries obtained at different scales (1 mL, 3 mL and 5 mL). Table 3 shows the recovery of cells without addition of buffer prior to centrifugation. The addition of buffer prior to centrifugation significantly improves CD3+ cell recoveries. The addition of buffer before antibody incubation, dilution of blood, negatively impacts the CD3+ cell recovery.

TABLE 1

Physicochemical properties of microbubbles (buoyant) reagent along with percent (%) recovery of target CD3+ cells.

| Microbubble volume ($\mu m^3$) | Microbubble diameter ($\mu m$) | Microbubble Concentration ($10^8$/mL) | Streptavidin Density (molecules/ $\mu m^2$) | Percent (%) Recovery of CD3+ Cells |
|---|---|---|---|---|
| 8.4 | 2.1 | 4.0 | 36000 | 94.2% |
| 6.0 | 1.8 | 11.0 | 19000 | 73.2% |
| 7.5 | 1.9 | 8.2 | 25000 | 84.4% |
| 7.1 | 1.8 | 7.8 | 30000 | 90.5% |
| 7.3 | 2.2 | 6.9 | 26500 | 96.1% |
| 7.2 | 2.4 | 5.6 | 26200 | 90.3% |
| 7.1 | 2.7 | 4.6 | 8400 | 72.5% |

TABLE 2

Percent (%) recovery of target CD3+ cells from whole peripheral blood at small scale (1 mL, 3 mL and 5 mL)

| Scale | PB Dilution | Buffer volume added per mL of blood prior to centrifugation | CD3 Recovery | CD3 Viability | CD3 Purity |
|---|---|---|---|---|---|
| 1 mL | None | 0.5 | 84% | 89% | 98% |
| 1 mL | None | 0.5 | 86% | 91% | 98% |
| 1 mL | None | 0.5 | 86% | 93% | 98% |
| 1 mL | None | 0.5 | 109% | 92% | 98% |
| 1 mL | None | 0.5 | 96% | 92% | 97% |
| 1 mL | None | 0.5 | 95% | 93% | 98% |
| 1 mL | Norse | 0.5 | 78% | 97% | 93% |
| 1 mL | Norse | 0.5 | 78% | 98% | 92% |
| 1 mL | None | 0.5 | 77% | 98% | 91% |
| 3 mL | None | 0.5 | 79% | 98% | 91% |
| 3 mL | None | 0.5 | 69% | 92% | 91% |
| 3 mL | None | 0.5 | 77% | 99% | 92% |
| 1 mL | None | 0.5 | 91% | 97% | 96% |
| 1 mL | None | 0.5 | 91% | 96% | 94% |
| 1 mL | None | 0.5 | 108% | 96% | 95% |
| 1 mL | None | 0.5 | 100% | 95% | 94% |
| 1 mL | None | 0.5 | 92% | 95% | 90% |
| 1 mL | None | 0.5 | 78% | 97% | 90% |
| 1 mL | None | 0.5 | 91% | 97% | 96% |
| 1 mL | None | 0.5 | 92% | 98% | 95% |
| 1 mL | None | 0.5 | 96% | 97% | 95% |
| 1 mL | None | 0.5 | 91% | 97% | 94% |
| 1 mL | None | 0.5 | 86% | 96% | 93% |
| 1 mL | None | 0.5 | 89% | 97% | 95% |
| 5 mL | None | 0.5 | 80% | 97% | 98% |
| 5 mL | None | 0.5 | 71% | 96% | 98% |
| 5 mL | None | 0.5 | 73% | 97% | 98% |
| 5 mL | None | 0.5 | 64% | 81% | 98% |
| 5 mL | None | 0.5 | 70% | 81% | 98% |
| 5 mL | None | 0.5 | 78% | 89% | 97% |
| | | Average | 85% | 94% | 95% |
| | | SD | 11% | 4% | 3% |

TABLE 3

Percent (%) recovery of target CD3+ cells from whole peripheral blood with different dilutions prior to antibody incubation at 3 mL scale.

| Scale | PB Dilution | Buffer volume added per mL of blood prior to centrifugation | CD3 Recovery | CD3 Viability | CD3 Purity |
|---|---|---|---|---|---|
| 3 mL | None | 0 | 66% | 97% | 92% |
| 3 mL | 1 to 1 | 0 | 74% | 98% | 95% |
| 3 mL | 1 to 2 | 0 | 75% | 98% | 95% |
| 3 mL | 1 to 4 | 0 | 66% | 98% | 92% |
| 3 mL | 1 to 8 | 0 | 55% | 98% | 85% |

We claim:
1. A method for isolating target cells from whole blood, comprising:
(a) mixing in an open container
(i) an undiluted whole blood sample having a volume of between 1 ml and 7.5 ml, and
(ii) binding agents, wherein each binding agent comprises (A) a primary binding agent comprising an antibody capable of binding to at least one cellular epitope on target cells in the undiluted whole blood sample, and (B) a first linker bound to the primary binding agent, wherein the first linker comprises a biotin linker,
wherein the mixing occurs for a time and under conditions suitable to promote binding of the primary binding agents to the target cells to generate binding agent-attached target cells in the undiluted whole blood sample;

(b) contacting the binding agent-attached target cells in the undiluted whole blood sample contained in the open container with a plurality of buoyant reagents, wherein each buoyant reagent comprises a second linker bound to the buoyant reagent, wherein the second linker comprises streptavidin, wherein the contacting occurs for a time and under conditions suitable to promote binding of the second linker to the first linker to generate an undiluted buoyant reagent-attached target cell mixture;

(c) diluting the undiluted buoyant reagent-attached target cell mixture contained in the open container by at least 20% to produce a diluted buoyant reagent-attached target cell mixture;

(d) applying a vectorial force to the diluted buoyant reagent-attached target cell mixture to generate a stratified diluted buoyant reagent-attached target cell mixture;

(e) removing the buoyant reagent-attached target cells from the stratified diluted buoyant reagent-attached target cell mixture; and isolating the target cells from the buoyant reagent-attached target cells; wherein the target cells are not platelets or red blood cells.

2. The method of claim 1, wherein the buoyant reagents comprise gas-filled bubbles.

3. The method of claim 2, wherein the gas-filled bubbles comprise perfluorocarbon gas cores encompassed by lipid or phospholipid shells.

4. The method of claim 2, wherein the gas-filled bubbles have a mean size volume of greater than 6 $\mu m^3$ and less than 10 $\mu m^3$.

5. The method of claim 2, wherein the gas-filled bubbles have a mean size diameter of between 1.5 $\mu m$ and about 3 $\mu m$.

6. The method of claim 2, wherein the gas-filled bubbles are present in the contacting step at a concentration of at least $4 \times 10^8$ per ml.

7. The method of claim 1, wherein the streptavidin is present on the buoyant reagent at a density of greater than 20,000 molecules per $um^2$.

8. The method of claim 1, wherein the streptavidin is present on the buoyant reagent at a density of greater than 25,000 molecules per $um^2$.

9. The method of claim 1, wherein the streptavidin is present on the buoyant reagent at a density of greater than 26,000 molecules per $um^2$.

10. The method of claim 1, wherein the undiluted whole blood sample has a volume of 1 ml to 5 ml.

11. The method of claim 1, wherein the undiluted whole blood sample has a volume of 1 ml to 3 ml.

12. The method of claim 1, wherein the diluting comprises diluting the undiluted buoyant reagent-attached target cell mixture by between 20% and 500% to produce the diluted buoyant reagent-attached target cell mixture.

13. The method of claim 1, wherein the removing step comprises removing the buoyant reagent-attached target cells from the stratified diluted buoyant reagent-attached target cell mixture using a pipette or syringe.

14. The method of claim 1, wherein the isolating step comprises isolating the target cells from the buoyant reagent-attached target cells by sonicating or applying positive pressure to degas the microbubbles.

15. The method of claim 1, wherein the target cells comprise cells of surface immunophenotypes comprising one or more of CD45+, CD3+, CD4+, CD8+, CD25+, CD14+, CD16+, CD19+, CD56+, CD34+, CD117+, CD235a, CD349$^-$, T cell receptor (TCR) alpha, gamma, beta & delta.

16. The method of claim 1, wherein the target cells comprise CD3$^+$ cells.

17. The method of claim 1, wherein the target cells are isolated with a purity of at least 85%.

18. The method of claim 1, wherein the target cells are isolated with a purity of at least 90%.

19. The method of claim 1, wherein the target cells are isolated with a viability of at least 80%.

20. The method of claim 1, wherein the target cells are isolated with a viability of at least 90%.

21. The method of claim 1, wherein at least 50% of the target cells in the whole blood sample are isolated.

22. The method of claim 1, wherein at least 70% of the target cells in the whole blood sample are isolated.

* * * * *